(12) United States Patent
Ling et al.

(10) Patent No.: US 7,189,711 B2
(45) Date of Patent: Mar. 13, 2007

(54) 2,3-BENZODIAZEPINE DERIVATIVES AND PHARMACEUTICAL COMPOSITIONS CONTAINING THE SAME AS THE ACTIVE INGREDIENT

(75) Inventors: István Ling, Budapest (HU); József Barkóczy, Budapest (HU); Gyula Simig, Budapest (HU); Zoltán Greff, Budapest (HU); Zoltán Rátkai, Budapest (HU); Géza Szabó, Budapest (HU); Miklós Végh, Budapest (HU); Gábor Gigler, Budapest (HU); Gábor Szénási, Budapest (HU); Bernadett Martonné Markó, Budapest (HU); György Lévay, Budakeszi (HU); László Gábor Hársing, Budapest (HU)

(73) Assignee: Egis Gyogyszergyar RT., Budapest (HU)

( * ) Notice: Subject to any disclaimer, the term of this patent is extended or adjusted under 35 U.S.C. 154(b) by 326 days.

(21) Appl. No.: 10/450,898

(22) PCT Filed: Dec. 19, 2001

(86) PCT No.: PCT/HU01/00151

§ 371 (c)(1),
(2), (4) Date: Oct. 27, 2003

(87) PCT Pub. No.: WO02/50044

PCT Pub. Date: Jun. 27, 2002

(65) Prior Publication Data

US 2004/0092510 A1 May 13, 2004

(30) Foreign Application Priority Data

Dec. 21, 2000 (HU) .................................... 0004994

(51) Int. Cl.
*A61P 25/00* (2006.01)
*A61K 31/55* (2006.01)
*C07D 243/02* (2006.01)

(52) U.S. Cl. ..................................... 514/221; 540/567
(58) Field of Classification Search ................ 514/221; 540/567
See application file for complete search history.

(56) References Cited

U.S. PATENT DOCUMENTS

| 4,614,740 A | 9/1986 | Tibor et al. .................. 514/221 |
| 5,807,851 A * | 9/1998 | Ling et al. .................. 514/221 |
| 6,200,970 B1 * | 3/2001 | Ling et al. .................. 514/221 |

FOREIGN PATENT DOCUMENTS

| WO | WO 97 28135 A | 8/1997 |
| WO | WO 97 34878 A | 9/1997 |
| WO | EP 0 802 195 A | 10/1997 |
| WO | WO 01 04122 A | 1/2001 |

* cited by examiner

*Primary Examiner*—Brenda Coleman
(74) *Attorney, Agent, or Firm*—Birch, Stewart, Kolasch & Birch, LLP

(57) ABSTRACT

The invention refers to novel 2,3-benzodiazepine derivatives of formula (I) and pharmaceutical compositions containing the same as the active ingredient. The novel compounds antipasmodic, muscle relaxant and neuroprotective activities. In formula I; X represents a hydrogen atom, a chloro atom or a methoxy group; Y stands for a hydrogen atom or a halo atom; Z means a methyl group or a chloro atom; R is a $C_{1-4}$ alkyl group or a group of the formula —$NR^1R_2$, wherein $R^1$ and $R^2$ represent, independently, a hydrogen atom, a $C_{1-4}$ alkyl group, a $C_{1-4}$ alkoxy group or a $C^{3-6}$ cycloalkyl group.

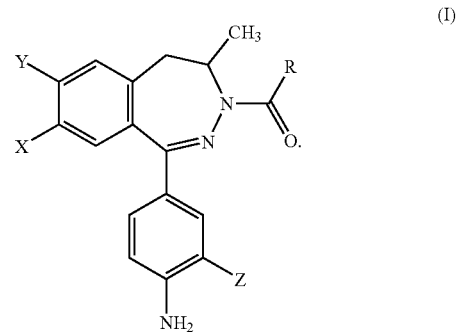

(I)

7 Claims, No Drawings

2,3-BENZODIAZEPINE DERIVATIVES AND PHARMACEUTICAL COMPOSITIONS CONTAINING THE SAME AS THE ACTIVE INGREDIENT

This application is the national phase under 35 U.S.C. § 371 of PCT International Application No. PCT/HU01/00151 which has an International filing date of Dec. 19, 2001, which designated the United States of America.

FIELD OF THE INVENTION

The invention refers to novel 2,3-benzodiazepine derivatives and pharmaceutical compositions containing the same as the active ingredient. Due to their non-competitive AMPA antagonist effect, the novel compounds have antispasmodic, muscle relaxant and neuroprotective activities.

BACKGROUND OF THE INVENTION

The most important stimulant neurotransmitter of the central nervous system consists of glutamic acid. The neurotransmitter receptors of glutamic acid can be divided into two groups: ionotropic receptors (i.e. receptors connected with an ionic channel) and metabotropic receptors. The ionotropic receptors take part in nearly each process of the central nervous system, for example in the processes of learning, in any type of memory, in processes accompanied by acute and chronic neuro-degeneration (or cellular destruction). The ionotropic receptors have role in pain sense, motoric function, urination reflex and cardiovascular homeostasis, too.

Two types of ionotropic stimulant receptors exist: the NMDA and the AMPA/kainate receptors. The receptors of AMPA/kainate type are, primarily, responsible for the so called fast synaptic processes, while the NMDA receptors regulate the slow synaptic processes prepared by the fast synaptic ones. Thus, antagonists of the AMPA/kainate receptors may have an indirect influence on the function of the NMDA receptors. Consequently, several processes of the central nervous system and the whole organism can be regulated by the antagonists of the AMPA/kainate receptors.

Two types of AMPA/kainate receptor antagonists exist: competitive and non-competitive antagonists. Because of the different character of inhibition, non-competitive antagonists are preferred to the competitive antagonists. The first representative of the non-competitive antagonists was 1-(4-aminophenyl)-4-methyl-7,8-methylenedioxy-5H-2,3-benzodiazepine synthetized about 15 years ago. Since the discovery of this compound numerous 2,3-benzodiazepines having non-competitive AMPA/kainate effect have been prepared [Donevan, S. D. et al., J. Pharmacol. Exp. Ther., 271, 25–29 (1994); Vizi, E. S. et al., CNS Drug Reviews, 2, 91–126 (1996)].

The therapeutical use of 2,3-benzodiazepines having non-competitive antagonist effect on the AMPA/kainate receptor is extremely various. They can be employed as a neuroprotective agent in case of different acute and chronic symptoms accompanied by neurodegeneration (Parkinson's disease, Alzheimer's disease, stroke etc.), furthermore for the improvement of many symptoms e.g. in epilepsy, spasmolysis, relief of pain, influencing emesis, schizophrenia, migraine and also as an anxiolytic agent [Tarnawa, I. and Vizi, E. S., Restorative Neurol. Neurosci., 13, 41–57 (1998)].

The Hungarian Patent Application No. P 97 00688 and the corresponding GB-P No. 2 311 779 described, among others, 1-(4-aminophenyl)-3-alkanoyl-4-methyl-3H-2,3-benzodiazepine derivatives that might have contained also a chloro atom in position 7 and/or 8. The known compounds have antispasmodic, muscle relaxant and neuroprotective activity and can be used for the treatment of neurological and psychiatric disorders.

The scope of compounds claimed in the above patent includes 2,3-benzodiazepines wherein the phenyl group being in position 1 contains, in addition to the amino group in position 4, also a halo atom or a $C_{1-4}$ alkyl group in position 3. However, such compounds have not been exemplified, and neither the identification data, nor the biological effect thereof have been described.

In our animal experiments it was found that during the metabolism that took place in the animal organism after the administration of the above known compounds, at first, the amino group being in position 4 at the phenyl group in position 1 was acetylated. (Further on, in the description, it is called N-acetylation). Due to N-acetylation, the therapeutical effect of the compounds is reduced. Since human beings can be of fast or slow acetylator phenotype, it is difficult to determine the proper therapeutical dose in the treatment. Therefore, the aim of the invention is to find 2,3-benzodiazepine derivatives characterized by decreased rate of acetylation since in this case human beings of fast and slow acetylator phenotype, respectively, can be treated with essentially the same dose of active ingredient.

SUMMARY OF THE INVENTION

It was found that the above aim is achieved by the novel 2,3-benzodiazepine derivatives of the formula

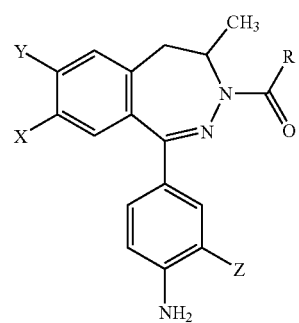

wherein
X represents a hydrogen atom, a chloro atom or a methoxy group,
Y stands for a hydrogen atom or a halo atom,
Z means a methyl group or a chloro atom,
R is a $C_{1-4}$ alkyl group or a group of the formula —$NR^1R^2$, wherein
  $R^1$ and $R^2$ represent, independently, a hydrogen atom, a $C_{1-4}$ alkyl group, a $C_{1-4}$ alkoxy group or a $C_{3-6}$ cycloalkyl group, and pharmaceutically suitable acid addition salts thereof.

DESCRIPTION OF THE PREFERRED EMBODIMENTS

It is surprising that the above aim could be achieved by the compounds of the invention wherein the phenyl group being in position 1 contained also a methyl group or a chloro atom in ortho position relative to the amino group in position 4 since the ortho substitution reduced the N-acetylation significantly. Due to the hindered N-acetylation, some effects of the novel compounds are stronger and longer lasting than those of the corresponding known compound in animal experiments.

Our experiences are supported by the following experiments in which the undermentioned novel compounds of the formula I and the corresponding 1-(4-aminophenyl) analogues as known reference compounds have been used:

1=compound of Example 1 i.e. 3-acetyl-1-(4-amino-3-methyl-phenyl)-4,5-dihydro-8-chloro-4-methyl-3H-2,3-benzo-diazepine, 1a=1-(4-aminophenyl) analogue i.e. 3-acetyl-1-(4-aminophenyl)-4,5-dihydro-8-chloro-4-methyl-3H-2,3-benzo-diazepine, 2=compound of Example 2 i.e. 1-(4-amino-3-methylphenyl)-4,5-dihydro-8-chloro-4-methyl-3-propionyl-3H-2,3-benzo-diazepine, 2a=1-(4-aminophenyl) analogue i.e. 1-(4-aminophenyl)-4,5-dihydro-8-chloro-4-methyl-3-propionyl-3H-2,3-benzo-diazepine, 3=compound of Example 3 i.e. 3-acetyl-1-(4-amino-3-chloro-phenyl)-4,5-dihydro-8-chloro-4-methyl-3H-2,3-benzo-diazepine, 3a=1-(4-aminophenyl) analogue i.e. 3-acetyl-1-(4-aminophenyl)-4,5-dihydro-8-chloro-4-methyl-3H-2,3-benzo-diazepine, 4=compound of Example 4 i.e. 3-acetyl-1-(4-amino-3-methyl-phenyl)-4,5-dihydro-7,8-dichloro-4-methyl-3H-2,3-benzo-diazepine, 4a=1-(4-aminophenyl) analogue i.e. 3-acetyl-1-(4-aminophenyl)-4,5-dihydro-7,8-dichloro-4-methyl-3H-2,3-benzo-diazepine, 5=compound of Example 5 i.e. 1-(4-amino-3-methylphenyl)-4,5-dihydro-7,8-dichloro-4-methyl-3-propionyl-3H-2,3-benzodiazepine, 5a=1-(4-aminophenyl) analogue i.e. 1-(4-aminophenyl)-4,5-dihydro-7,8-dichloro-4-methyl-3-propionyl-3H-2,3-benzo-diazepine.

Reduction of the rate of N-acetylation due to ortho substitution

Liver slices of Wistar rats were incubated in oxigenized Krebs-Ringer solution at 37° C. in the presence of 50 µM of 2,3-benzodiazepine derivative examined. 0.5 ml aliquots were taken at the beginning of the examination, then after 30 and 60 minutes. Plasma proteins were precipitated with perchloric acid and, after alkalization, the 2,3-benzodiazepine derivatives were extracted with chloroform. The chloroform solutions were evaporated to dryness, the residue was dissolved in the corresponding eluent. The 2,3-benzodiazepine derivative used and the N-acetyl metabolite thereof were determined by high pressure liquid chromatography (Beckman System Gold HPLC, C-18 reversed-phase column) using an UV detector (at 240 nm). Different eluents were used for the optimal separation of the compounds. In case of the compound according to Example 1 and the corresponding 1-(4-amino-phenyl) analogue, the eluent consisted of a mixture of 50% of 2 mM heptafluorobutyric acid, 25% of methanol and 25% of acetonitrile. For the compound according to Example 3 and the corresponding 1-(4-amino-phenyl) analogue, the eluent was a mixture of 50% of 2 mM heptafluorobutyric acid, 20% of methanol and 30% of acetonitrile. For the compound according to Example 4 and the corresponding 1-(4-amino-phenyl) analogue, the eluent consisted of a mixture of 50% of 2 mM heptafluorobutyric acid and 50% of acetonitrile.

The percentage of N-acetyl metabolite content of the sample taken at a certain time was calculated by dividing the hundredfold of the peak area of the metabolite with the sum of the peak areas of the 2,3-benzodiazepine derivative used and the N-acetyl metabolite. The results obtained are shown in Table 1 in which the concentrations determined after 0, 30 and 60 minutes are indicated.

TABLE 1

| Compound used (Example No.) | Incubation time in min. | Amount of N-acetyl metabolite in % |
|---|---|---|
| 1 | 0 | 0 |
| 1 | 30 | 2 |
| 1 | 60 | 6 |
| 1a | 0 | 0 |
| 1a | 30 | 18 |
| 1a | 60 | 31 |
| 3 | 0 | 0 |
| 3 | 30 | 1 |
| 3 | 60 | 1 |
| 3a | 0 | 0 |
| 3a | 30 | 18 |
| 3a | 60 | 31 |
| 4 | 0 | 0 |
| 4 | 30 | 0 |
| 4 | 60 | 4 |
| 4a | 0 | 0 |
| 4a | 30 | 17 |
| 4a | 60 | 31 |

From Table 1 it can be seen that the compounds of the formula I examined are N-acetylated only at a negligible rate in 1 hour, in contrast to the corresponding 1-(4-aminophenyl) analogues wherein the amount of the N-acetyl metabolite is, in general, 31% in 1 hour. Thus, the presence of a methyl group or a chloro atom in ortho position relative to the amino group inhibits the N-acetylation of the amino group significantly.

Neuroprotective Effect in Magnesium Chloride Induced Global Cerebral Ischemia in Mice The examination was carried out on groups consisting of 10 male NMRI mice weighing 20–25 g. The compounds to be examined were dissolved in a mixture of 5 volumes of 5M aqueous hydrochloric acid and 95 volumes of water, then the pH value of the solution was adjusted to 3 by the addition of 1M aqueous sodium hydroxide solution. The solution obtained was administered intraperitoneally in a volume of 10 ml/kg. Each compound was tested at four increasing dose levels, and a further group of animals was treated only with the vehicle (the latter was the control group). 30 minutes after treatment, all mice received an intravenous injection of saturated aqueous magnesium chloride solution in a volume of 5 ml/kg. This injection caused an immediate cardiac arrest and complete cerebral ischemia. The increase in survival time (i.e. the interval between the injection of magnesium chloride and the last observable gasp) was considered as a measure of the neuroprotective effect according to Berga et al. [Berga, P. et al., Synergistic interactions between piracetam and dihydroergocristine in some animal models of cerebral hypoxia and ischaemia, Arzneim. -Forsch., 36, 1314–1320 (1986)]. Percentage changes in survival time were calculated in comparison to that measured in the control group, and, from the values obtained, the dose prolonging survival by 50% ($PD_{50}$) was calculated by linear regression analysis. The results obtained are shown in Table 2.

TABLE 2

| Compound (Example No.) | $PD_{50}$, in mg/kg |
|---|---|
| 1 | 4.6 |
| 1a | 10.4 |
| 4 | 9.0 |
| 4a | 11.0 |
| 5 | 12.3 |
| 5a | 14.6 |

From Table 2 it can be seen that the $PD_{50}$ value of the compounds of the formula I examined is lower than that of the corresponding 1-(4-aminophenyl) analogues. This means that the substituent being in ortho position relative to the amino group enhances the neuroprotective effect of the compounds.

Duration of Action in Rats as Assessed From the Decrease in Body Core Temperature One week prior to treatments, 6 male Wistar rats were anaesthetized by administering 60 mg/kg of pentobarbital sodium [sodium 5-ethyl-5-(1-methylbutyl)barbiturate]intraperitoneally. Using sterile surgical procedures, TL11M2C50-PXT or TA10TA-F40 type radiotelemetry transmitters (Data Sciences International, St. Paul, Minn., USA) were implanted into the peritoneal cavity of the animals. The transmitters permitted continuous monitoring of the core body temperature. After implantation, the rats were treated with an antibiotic (benzathine-benzylpenicillin was administered in a dose of 1 ml/kg i.m.). [The chemical name of benzathine-benzylpenicillin: [2S-(2α,5α,6β)]-3,3-dimethyl-7-oxo-6-[(phenoxyacetyl)amino]-4-thia-1-azabicyclo[3.2.0]heptane-2-carboxylic acid]. The animals were housed individually in type 2 plastic rat cages with free access to food and tap water.

The compounds to be examined were dissolved in a mixture of 5 volumes of 5M aqueous hydrochloric acid and 95 volumes of water, then the pH value of the solution was adjusted to 3 by the addition of 1M aqueous sodium hydroxide solution. The solution obtained was administered intraperitoneally in a volume of 10 ml/kg.

Radio signals emitted by the transmitters were detected by RLA1000 or RLA2000 type receivers placed under each cage. Data were collected and saved by a Dataquest IV computerized data acquisition system. The computer was set to sample body temperature for 10 seconds in every second minute. Mean values for 30 min. periods over the whole day were calculated running the "sort utility" of the Dataquest IV system. The upper and lower limits of the evaluating routine were set to exclude biologically improbable values. Individual body temperature curves were averaged for the 6 animals.

Peak effect (PE) was measured as the maximum decrease in body temperature in comparison to the last value prior to treatment (control value). The PE values obtained are summarized in Table 3. Using the mean values, duration of action (D) of the compounds was determined. This is the time interval from treatment to return of body temperature to the control level. Values of D obtained are shown in Table 4.

TABLE 3

| Compound (Example No.) | PE, Δ° C. |
|---|---|
| 1 | −2.34 |
| 1a | |
| 2 | −2.04 |
| 2a | −1.87 |
| 4 | −3.09 |
| 4a | −1.72 |

TABLE 4

| Compound (Example No.) | D in hour |
|---|---|
| 1 | 20 |
| 1a | |
| 2 | 6 |
| 2a | 4 |
| 4 | 19 |
| 4a | 3.5 |

From the data of Tables 3 and 4 it can be seen that the maximum decrease in body temperature is larger and the duration of action is longer in case of the compounds containing a substituent in ortho position relative to the amino group. This means that the effect of the compounds of the formula I is stronger and longer lasting than that of the known compounds.

The compounds of the formula I have antispasmodic, muscle relaxant and neuroprotective activities, and can be potentially used in the treatment or prevention of any disease and symptom wherein the inhibition of the stimulant amino acid receptors is beneficial. Thus, the compounds of the invention can be advantageously employed in any case wherein the AMPA/kainate non-competitive 2,3-benzodiazepine type antagonists are efficient, for example in the following diseases:

as a neuroprotective agent in symptoms accompanied by acute and chronic neurodegeneration, especially Parkinson's disease, Alzheimer's disease, amyotrophic lateral sclerosis, stroke, acute head injury, furthermore for improving numerous symptoms for example in epilepsy, spasmolysis, relief of pain, in influencing emesis, in schizophrenia, in case of migraine and urination problems as well as for relieving the symptoms of medicine deprivation.

In the description and claims, under a halo atom especially a fluoro atom, chloro atom, bromo atom or iodo atom, preferably a chloro atom is meant.

A $C_{1-4}$ alkyl group is a methyl group, ethyl group, isopropyl group, n-propyl group, n-butyl group, sec-butyl group, isobutyl group or tert.-butyl group, preferably a methyl group or ethyl group.

A $C_{1-4}$ alkoxy group is, in general, a methoxy group, ethoxy group, isopropoxy group, n-propoxy group or n-butoxy group, preferably a methoxy group.

A $C_{3-6}$ cycloalkyl group is, mostly, a cyclopropyl group, cyclopentyl group or cyclohexyl group.

The pharmaceutically suitable acid addition salts of the 2,3-benzodiazepine derivatives of the formula I are the non-toxic acid addition salts of the compounds formed with inorganic acids such as hydrochloric acid, hydrobromic acid, sulfuric acid, phosphoric acid etc. or organic acids such as formic acid, acetic acid, fumaric acid, lactic acid, tartaric acid, succinic acid, citric acid, benzenesulfonic acid, p-toluenesulfonic acid, methane-sulfonic acid etc.

Due to the presence of a chiral centre, the compounds of the formula I can be present in the form of optically active isomers and mixtures thereof. In the presence of certain substituents, geometrical isomerism or tautomerism may exist in the compounds of the formula I. The invention includes all the isomers of the 2,3-benzodiazepine derivatives of the formula I and any mixtures thereof.

Preferred 2,3-benzodiazepine derivatives are those wherein in formula I
X represents a chloro atom,
Y stands for a hydrogen atom, a chloro atom or a bromo atom,
R means a $C_{1-4}$ alkyl group,
Z is a methyl group or a chloro atom,
and pharmaceutically suitable acid addition salts thereof.

The especially preferred 2,3-benzodiazepine derivatives are those wherein in formula I
X means a chloro atom,
Y represents a hydrogen atom or a chloro atom,
R stands for a methyl group,
Z is a methyl group or a chloro atom,
and pharmaceutically suitable acid addition salts thereof.

The compounds of the formula I can be prepared by the processes known from Hungarian Patent Application No. P 97 00688. Suitably, a compound of the formula I, wherein the amino group is replaced by a nitro group, is reduced in a manner known per se, for example with tin(II) chloride, sodium dithionite or by catalytical hydrogenation in the presence of a Raney nickel, palladium or platina catalyst using gaseous hydrogen, hydrazine, hydrazine hydrate, formic acid, a trialkylammonium formate or a sodium formate as the hydrogen source. The compound of the formula I, wherein the amino group is replaced by a nitro group, can be also prepared by the processes known from the Hungarian Patent Application No. P 97 00688.

Furthermore, the invention refers to a pharmaceutical composition containing a 2,3-benzodiazepine derivative of the formula I or a pharmaceutically suitable acid addition salt thereof as the active ingredient and one or more conventional carrier(s).

The pharmaceutical composition of the invention contains, in general, 0.1 to 95 per cent by mass, preferably 1 to 50 per cent by mass, suitably 5 to 30 per cent by mass of the active ingredient.

The pharmaceutical composition of the invention is suitable for peroral, parenteral or rectal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinylpyrrolidone) etc.; filling agents such as lactose, glucose, starch, calcium phosphate etc.; auxiliary substances for tabletting such as magnesium stearate, talc, poly(ethylene glycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propylene glycol, ethanol etc.; preservatives such as methyl p-hydroxybenzoate etc. as the carrier.

Pharmaceutical compositions suitable for parenteral administration consist of sterile solutions of the active ingredient, in general.

Dosage forms listed above as well as other dosage forms are known per se, see e.g. Remington's Pharmaceutical Sciences, 18th Edition, Mack Publishing Co., Easton, USA (1990).

The pharmaceutical composition contains dosage unit, in general. A typical dose for adult patients amounts to 0.1 to 1000 mg of the compound of the formula I or a pharmaceutically suitable acid addition salt thereof calculated for 1 kg body weight, daily. The daily dose can be administered in one or more portions. The actual dosage depends on many factors and is determined by the doctor.

The pharmaceutical composition is prepared by admixing a compound of the formula I or a pharmaceutically suitable acid addition salt thereof to one or more carrier(s), and converting the mixture obtained to a pharmaceutical composition in a manner known per se. Useful methods are known from the literature, e.g. Remington's Pharmaceutical Sciences mentioned above.

A preferred pharmaceutical composition of the invention contains a 2,3-benzodiazepine derivative of the formula I, wherein
X represents a chloro atom,
Y stands for a hydrogen atom, a chloro atom or a bromo atom,
R means a $C_{1-4}$ alkyl group,
Z is a methyl group or a chloro atom, or a pharmaceutically suitable acid addition salt thereof as the active ingredient.

The active ingredient of an especially preferred pharmaceutical composition of the invention is a 2,3-benzodiazepine derivative of the formula I, wherein
X means a chloro atom,
Y represents a hydrogen atom or a chloro atom,
R stands for a methyl group,
Z is a methyl group or a chloro atom, or a pharmaceutically suitable acid addition salt thereof.

Furthermore, the invention refers to the use of the compounds of the formula I or pharmaceutically suitable acid addition salts thereof for the preparation of a pharmaceutical composition of anxiolytic effect or suitable for the treatment of symptoms accompanied by acute and chronic neurodegeneration, especially Parkinson's disease, Alzheimer's disease, amyotrophic lateral sclerosis, stroke, acute head injury, epilepsy and schizophrenia, for spasmolysis, relief of pain, influencing emesis, against migraine, for the treatment of urination problems or for relieving the symptoms of medicine deprivation.

Likewise, the invention refers to a process for the treatment of diseases and symptoms listed above in which a therapeutically effective amount of a 2,3-benzodiazepine derivative of the formula I or a pharmaceutically suitable acid addition salt thereof is administered to a patient being in need of the treatment.

The invention is further elucidated by means of the following Examples.

EXAMPLE 1

(±)-3-Acetyl-1-(4-amino-3-methylphenyl)-4,5-dihydro-8-chloro-4-methyl-3H-2,3-benzodiazepine 3.7 g (10 mmoles) of (±)-3-acetyl-4,5-dihydro-8-chloro-4-methyl-1-(3-methyl4-nitrophenyl)-3H-2,3-benzodiazepine are dissolved in a mixture of 75 cm³ of methanol and 38 cm³ of dichloromethane, then 3.0 g of wet Raney nickel catalyst and, under vigorous stirring, 1.7 cm³ (35 mmoles) of 98% hydrazine hydrate are added. The reaction mixture is stirred for further 45 minutes, the catalyst is filtered, washed with dichloromethane, the filtrate is evaporated, and the residue is rubbed with 50 cm³ of water to obtain solid matter. The crude product is purified by chromatography over a column containing silica gel and using a mixture of ethyl acetate and hexane, then the product is recrystallized from ethanol. Thus, 1.67 g (49%) of the title compound are obtained in the form of pale yellow solids melting at 180–182° C.

Analysis: for $C_{19}H_{20}ClN_3O$ (341.844)
calculated: C, 66.76%; H 5.90%; N 12.29%; Cl 10.37%.
found: C 66.77%; H 5.92%; N 12.13%; Cl 10.13%.
$^1$H-NMR (CDCl₃): δ 7.48 (d, J=1.3 Hz, 1H), 7.35 (dd, $J_1$=2.1 Hz, $J_2$=8.1 Hz, 1H), 7.28 (dd, $J_1$=2.0 Hz, $J_2$=8.2 Hz, 1H), 7.22 (d, J=8.2 Hz, 1H), 7.12 (d, J=2.2 Hz, 1H), 6.67 (d, J=8.3 Hz, 1H), 5.21 (m, 1H), 4.01 (bs, 2H), 2.79 (dd, $J_1$=5.5 Hz, $J_2$=13.7 Hz, 1H), 2.65 (dd, $J_1$=12.0 Hz, $J_2$=13.6 Hz, 1H), 2.20 (s, 3H), 2.02 (s, 3H), 1.30 (d, J=6.4 Hz, 3H).
$^{13}$C-NMR (CDCl₃): δ 172.14, 169.21, 148.14, 138.46, 135.83, 132.35, 131.43, 130.27, 129.40, 129.24, 128.72, 125.45, 121.79, 114.03, 60.47, 38.28, 22.60, 18.32, 17.32.

EXAMPLE 2

(±)-1-(4-Amino-3-methylphenyl)-4,5-dihydro-8-chloro-4-methyl-3-propionyl-3H-2,3-benzodiazepine 3.86 g (10 mmoles) of (±)-4,5-dihydro-8-chloro-4-methyl-1-(3-methyl-4-nitrophenyl)-3-propionyl-3H-2,3-benzodiazepine are dissolved in a mixture of 80 cm³ of methanol and 13 cm³ of dichloromethane, then 3.0 g of wet Raney nickel catalyst and, under vigorous stirring, 1.7 cm³ (35 mmoles) of 98% hydrazine hydrate are added. The reaction mixture is stirred for further 45 minutes, the catalyst is filtered, washed with dichloromethane, the filtrate is evaporated, and the residue is rubbed with 50 cm³ of water to obtain solid matter. The crude product is purified by chromatography over a column containing silica gel and using a mixture of ethyl acetate and hexane, then the product is recrystallized from acetonitrile. Thus, 1.99 g (56%) of the title compound are obtained in the form of cream coloured solids melting at 152–154° C.

$^1$H-NMR (CDCl₃): δ 7.47 (d, J=1.1 Hz, 1H), 7.34 (dd, $J_1$=2.1 Hz, $J_2$=8.1 Hz, 1H), 7.29 (dd, $J_1$=2.0 Hz, $J_2$=8.2 Hz, 1H), 7.22 (d, J=8.2 Hz, 1H), 7.10 (d, J=2.2 Hz, 1H), 6.67 (d, J=8.3 Hz, 1H), 5.21 (m, 1H), 4.01 (bs, 2H), 2.78 (dd, $J_1$=5.6 Hz, $J_2$=13.7 Hz, 1H), 2.66 (~t, J=12.9 Hz, 1H), 2.47 (m, 1H), 2.20 (m, 1H), 2.20 )s, 3H), 1.30.(d, J=6.4 Hz, 3H), 1.04 (t, J=7.5 Hz, 3H).
$^{13}$C-NMR (CDCl₃): δ 172.46, 172.20, 154.48, 148.11, 138.54, 135.94, 132.27, 131.39, 130.19, 129.36, 129.19, 128.60, 125.48, 121.76, 114.03, 60.58, 38.29, 27.90, 18.34, 17.33, 8.77.

EXAMPLE 3

(±)-3-Acetyl-1-(4-amino-3-chlorophenyl)-4,5-dihydro-8-chloro-4-methyl-3H-2,3-benzodiazepine 3.93 g (10 mmoles) of (±)-3-acetyl-4,5-dihydro-8-chloro-1-(3-chloro-4-nitrophenyl)-4-methyl-3H-2,3-benzodiazepine are dissolved in a mixture of 30 cm³ of methanol and 30 cm³ of dichloromethane, then 3.0 g of wet Raney nickel catalyst and, under vigorous stirring, 1.7 cm³ (35 mmoles) of 98% hydrazine hydrate are added. The reaction mixture is stirred for further 45 minutes, the catalyst is filtered, washed with dichloromethane, the filtrate is evaporated, and the residue is rubbed with 50 cm³ of water to obtain solid matter. The crude product is purified by chromatography over a column containing silica gel and using a mixture of ethyl acetate and hexane, then the product is recrystallized from a mixture of ethyl acetate and hexane. Thus, 1.03 g (30%) of the title compound are obtained in the form of yellow solids melting at 143–144° C.

Analysis: for $C_{18}H_{17}Cl_2N_3O$ (362.262)
calculated: C 59.68%; H 4.73%, N 11.60%; Cl 19.57%.
found: C 59.09%; H 4.85%; N 11.24%; Cl 19.11%.
$^1$H-NMR (CDCl₃): δ 7.65 (d, J=1.9 Hz, 1H), 7.35 (m, 2H), 7.23 (d, J=8.2 Hz, 1H), 7.11 (d, J=2.1 Hz, 1H), 6.78 (d, J=8.4 Hz, 1H), 5.23 (m, 1H), 4.44 (bs, 2H), 2.83 (dd, $J_1$=5.1 Hz, $J_2$=13.9 Hz, ₁ H), 2.66 (dd, $J_1$=11.4 Hz, $J_2$=13.8 Hz, 1H), 2.06 (s, 3H), 1.26 (d, J=6.4 Hz, 3H).
$^{13}$C-NMR (CDCl₃): δ 169.88, 168.02, 145.71, 138.52, 135.15, 132.54, 130.47, 130.37, 129.69, 129.27, 128.69, 126.81, 119.01, 114.88, 60.31, 38.21, 22.68, 18.44.

EXAMPLE 4

(±)-3-Acetyl-1-(4-amino-3-methylphenyl)-4,5-dihydro-7,8-dichloro-4-methyl-3H-2,3-benzodiazepine 4.06 g (10 mmoles) of (±)-3-acetyl-4,5-dihydro-7,8-dichloro-1-(3-methyl-4-nitrophenyl)-4-methyl-3H-2,3-benzodiazepine are dissolved in a mixture of 55 cm³ of methanol and 55 cm³ of dichloromethane, then 3.0 g of wet Raney nickel catalyst and, under vigorous stirring, 1.7 cm³ (35 mmoles) of 98% hydrazine hydrate are added. The reaction mixture is stirred for further 45 minutes, the catalyst is filtered, washed with dichloromethane, the filtrate is evaporated, and the residue is rubbed with 50 cm³ of water to obtain solid matter. The crude product is recrystallized from a mixture of ethyl acetate and hexane. Thus, 3.27 g (87%) of the title compound are obtained in the form of yellow ochre solids melting at 127–129° C.

Analysis: for $C_{19}H_{19}Cl_2N_3O$ (376.289)
calculated: C 60.65%; H 5.09%; N 11.17%; Cl 18.84%.
found: C 59.74%; H 5.07%; N 10.98%; Cl 18.62%.
$^1$H-NMR (CDCl₃): δ 7.45 (~s, 1H), 7.39 (s, 1H), 7.28 (dd, $J_1$=2.0 Hz, $J_2$=8.2 Hz, 1H), 7.22 (s, 1H), 6.77 (d, J=8.3 Hz, 1H), 5.23 (m, 1H), 4.02 (bs, 2H), 2.77 (dd, $J_1$=5.5 Hz, $J_2$=13.8 Hz, 1H), 2.65 (dd, $J_1$=11.8 Hz, $J_2$=13.5 Hz, 1H), 2.20 (s, 3H), 2.03 (s, 3H), 1.29 (d, J=6.4 Hz, 3H).
$^{13}$C-NMR (CDCl₃): δ 169.40, 148.25, 139.93, 134.23, 134.08, 131.42, 130.73, 130.56, 129.93, 129.15, 125.24, 121.86, 114.09, 60.07, 38.10, 22.60, 13.80, 17.32.

EXAMPLE 5

(±)-1-(4-Amino-3-methylphenyl)-4,5-dihydro-7,8-dichloro-4-methyl-3-propionyl-3H-2,3-benzodiazepine 4.2 g (10 mmoles) of (±)-4,5-dihydro-7,8-dichloro-4-methyl-1-(3-methyl-4-nitrophenyl)-3-propionyl-3H-2,3-benzodiazepine are dissolved in a mixture of 40 cm³ of methanol and 40 cm³ of dichloromethane, then 3.0 g of wet Raney nickel catalyst and, under vigorous stirring, 1.7 cm³ (35 mmoles) of 98% hydrazine hydrate are added. The reaction mixture is stirred for further 45 minutes, the catalyst is filtered, washed with dichloromethane, the filtrate is evaporated, and the residue is rubbed with 50 cm³ of water to obtain solid matter. The crude product is purified by chromatography over a column containing silica gel and using a mixture of ethyl acetate and hexane, then the product is recrystallized from acetonitrile. Thus, 1.99 g (56%) of the title compound are obtained in the form of pale yellow solids melting at 106–108° C.

Analysis: for $C_{20}H_{21}Cl_2N_3O$ (390.316)
calculated: C 61.55%; H 5.42%; N 10.77%; Cl 18.17%.
found: C 60.68%; H 5.52%; N 10.47%; Cl 17.90%.
$^1$H-NMR (CDCl$_3$): δ 7.45 (d, J=1.1 Hz, 1H), 7.39 (s, 1H), 7.28 (dd, J$_1$=2.1 Hz, J$_2$=8.3 Hz, 1H), 7.21 (s, 1H), 6.67 (d, J=8.3 Hz, 1H), 5.22 (m, 1H), 4.02 (bs, 2H), 2.77 (dd, J$_1$=5.6 Hz, J$_2$=13.8 Hz, 1H), 2.64 (dd, J$_1$=11.9 Hz, J$_2$=13.6 Hz, 1H), 2.47 (m, 1H), 2.20 (m, 1H), 2.20 (s, 3H), 1.30 (d, J=6.4 Hz, 3H), 1.04 (t, J=7.5 Hz, 3H).
$^{13}$C-NMR (CDCl$_3$): δ 172.63, 171.10, 148.22, 140.02, 134.20, 131.40, 130.66, 130.44, 129.90, 129.12, 125.28, 121.86, 114.10, 60.21, 38.12, 27.92, 18.32, 17.34, 8.77.

EXAMPLE 6

(±)-3-Acetyl-1-(4-amino-3-chlorophenyl)-4,5-dihydro-7,8-dichloro-4-methyl-3H-2,3-benzodiazepine 4.26 g (10 mmoles) of (±)-3-acetyl-4,5-dihydro-7,8-dichloro-1-(3-chloro-4-nitrophenyl)-4-methyl-3H-2,3-benzodiazepine are dissolved in a mixture of 40 cm$^3$ of methanol and 40 cm$^3$ of dichloromethane, then 3.0 g of wet Raney nickel catalyst and, under vigorous stirring, 1.7 cm$^3$ (35 mmoles) of 98% hydrazine hydrate are added. The reaction mixture is stirred for further 45 minutes, the catalyst is filtered, washed with dichloromethane, the filtrate is evaporated, and the residue is rubbed with 50 cm$^3$ of water to obtain solid matter. The crude product is recrystallized from acetonitrile. Thus, 2.80 g (71%) of the title compound are obtained in the form of butter coloured solids melting at 127–129° C.

Analysis: for $C_{18}H_{16}C_3N_3O$ (396.707)
calculated: C 54.50%; H 4.07%; N 10.59%; Cl 26.81%.
found: C 54.26%; H 4.14%; N 10.48%; Cl 26.28%.
$^1$H-NMR (CDCl$_3$): δ 7.62 (d, J=1.9 Hz, 1H), 7.39 (s, 1H), 7.32 (dd, J$_1$=2.0 Hz, J$_2$=8.4 Hz, 1H), 7.22 (s, 1H), 6.77 (d, J=8.4 Hz, 1H), 5.25 (m, 1H), 4.48 (bs, 2H), 2.82 (dd, J$_1$=5.1 Hz, J$_2$=13.9 Hz, 1H), 2.66 (dd, J$_1$=11.2 Hz, J$_2$=13.8 Hz, 1H), 2.07 (s, 3H), 1.25 (d, J=6.4 Hz, 3H).
$^{13}$C-NMR (CDCl$_3$): δ 170.03, 166.60, 145.80, 139.93, 134.45, 133.34, 130.88, 130.52, 130.29, 130.18, 129.17, 126.53, 119.00, 114.88, 59.79, 37.99, 22.68, 18.42.

EXAMPLE 7

(±)-3-Acetyl-1-(4-amino-3-methylphenyl)-4,5-dihydro-4-methyl-8-methoxy-3H-2,3-benzodiazepine 4.46 g (10 mmoles) of (±)-3-acetyl-7-bromo4,5-dihydro-1-(3-methyl-4-nitrophenyl)-4-methyl-8-methoxy-3H-2,3-benzo-diazepine are dissolved in 190 cm$^3$ of methyl cellosolve, then 2.1 g (15 mmoles) of potassium carbonate and 1.8 g of 10% palladium/charcoal catalyst and, under vigorous stirring, 1.95 cm$^3$ (40 mmoles) of 98% hydrazine hydrate are added. The reaction mixture is stirred at 100° C. for 1 hour, the catalyst is filtered, the filtrate is evaporated, and the residue is rubbed with 50 cm$^3$ of water to obtain solid matter. The crude product is purified by chromatography over a column containing silica gel and using a mixture of ethyl acetate and hexane, then the product is recrystallized from acetonitrile. Thus, 1.6 g (47%) of the title compound are obtained in the form of cream coloured solids melting at 169–171° C.

Analysis: for $C_{20}H_{23}N_3O_2$ (337.425)
calculated: C 71.19%; H 6.87%; N 12.45%.
found: C 71.69%; H 6.74%; N 12.34%.
$^1$H-NMR (CDCl$_3$): δ 67.51 (bs, 1H), 7.33 (dd, J$_1$=1.8 Hz, J$_2$=8.1 Hz, 1H), 7.19 (d, J=8.4 Hz, 1H), 6.91 (dd, J$_1$=2.9 Hz, J$_2$=8.4 Hz, 1H), 6.65 (d, J=8.1 Hz, 1H), 6.65 (d, J=2.6 Hz, 1H), 5.18 (m, 1H), 3.97 (bs, 2H), 2.72 (m, 1H), 2.61 (m,1H), 2.19 (s, 3H), 2.01 (s, 3H), 1.31 (d, J=6.6 Hz, 3H).
$^{13}$C-NMR (CDCl$_3$): δ 168.89, 158.06, 147.91, 135.19, 132.25, 131.59, 129.36, 129.02, 125.98, 121.67, 115.67, 114.79, 114.00, 60.69, 55.49, 38.03, 22.59, 18.32, 17.29.

EXAMPLE 8

(±)-3-Acetyl-1-(4-amino-3-chlorophenyl)-4,5-dihydro-4-methyl-8-methoxy-3H-2,3-benzodiazepine 4.66 g (10 mmoles) of (±)-3-acetyl-7-bromo-4,5-dihydro-1-(3-chloro-4-nitrophenyl)-4-methyl-8-methoxy-3H-2,3-benzo-diazepine are dissolved in 190 cm$^3$ of methyl cellosolve, then 2.1 g (15 mmoles) of potassium carbonate and 1.8 g of 10% palladium/charcoal catalyst and, under vigorous stirring, 1.95 cm$^3$ (40 mmoles) of 98% hydrazine hydrate are added. The reaction mixture is stirred at 90° C. for 0.5 hours, the catalyst is filtered, the filtrate is evaporated, and the residue is rubbed with 50 cm$^3$ of water to obtain solid matter. The crude product is purified by chromatography over a column containing silica gel and using a mixture of ethyl acetate and hexane, then the product is recrystallized from ethanol. Thus, 1.1 g (30%) of the title compound are obtained in the form of white solids melting at 152–155° C.

Analysis: for $C_{19}H_{20}ClN_3O_2$ (357.840)
calculated: C 63.77%; H 5.63%; N 11.74%; Cl 9.91%.
found: C 63.70%; H 5.61%; N 11.51%; Cl 9.86%.
$^1$H-NMR (CDCl$_3$): δ 7.67 (d, J=1.8 Hz, 1 H), 7.41 (dd, J$_1$=1.8 Hz, J$_2$=8.1 Hz, 1H), 7.20 (d, J=8.4 Hz, 1 H), 6.93 (dd, J$_1$=2.6 Hz, J$_2$=8.1 Hz, 1H), 6.77 (d, J=8.4 Hz, 1H), 6.64 (d, J=2.9 Hz, 1H), 5.20 (m, 1H), 4.46 (bs, 2H), 3.75 (s, 3H), 2.80 (dd, J$_1$=5.1 Hz, J$_2$=13.9 Hz, 1H), 2.63 (dd, J$_1$=11.7 Hz, J$_2$=13.9 Hz, 1H), 2.05 (s, 3H), 1.29 (d, J=6.2 Hz, 3H).
$^{13}$C-NMR (CDCl$_3$): δ 158.12, 145.56, 134.48, 132.25, 130.55, 129.38, 129.28, 118.86, 115.84, 114.80, 114.68, 60.66, 55.49, 37.91, 22.67, 18.42.

EXAMPLE 9

(±)-3-Acetyl-1-(4-amino-3-methylphenyl)-4,5-dihydro-7-chloro-4-methyl-3H-2,3-benzodiazepine 3.7 g (10 mmoles) of (±)-3-acetyl-4,5-dihydro-7-chloro-1-(3-methyl-4-nitrophenyl)-4-methyl-3H-2,3-benzodiazepine are dissolved in a mixture of 80 cm$^3$ of methanol and 33 cm$^3$ of dichloromethane, then 3.0 g of wet Raney nickel catalyst and, under vigorous stirring, 1.7 cm$^3$ (35 mmoles) of 98% hydrazine hydrate are added. The reaction mixture is stirred for further 45 minutes, the catalyst is filtered, washed with dichloromethane, the filtrate is evaporated, and the residue is rubbed with 50 cm$^3$ of water to obtain solid matter. The crude product is recrystallized from a 1:2 mixture of ethyl acetate and hexane. Thus, 2.88 g (84%) of the title compound are obtained in the form of yellow ochre solids melting at 200–205° C.

Analysis: for $C_{19}H_{20}ClN_3O$ (341.844)
calculated: C 66.76%; H 5.90%; N 12.29%; Cl 10.37%.
found: C 65.63%; H 6.07%; N 12.03%; Cl 10.58%.

$^1$H-NMR (CDCl$_3$): δ 7.45 (s, 1H), 7.28 (m, 3H), 7.07 (d, J=8.2 Hz, 1H), 6.66 (d, J=8.2 Hz, 1H), 5.24 (m, 1H), 4.00 (bs, 2H), 2.77 (dd, J$_1$=5.6 Hz, J$_2$=13.7 Hz, 1H), 2.68 (t, J=12.8 Hz, 1H), 2.18 (s, 3H), 2.01 (s, 3H), 1.31 (d, J=6.3 Hz, 3H).

$^{13}$C-NMR (CDCl$_3$): δ 172.54, 169.11, 148.08, 141.85, 136.09, 132.62, 131.54, 130.32, 129.16, 128.22, 126.63, 125.68, 121.69, 114.00, 60.30, 38.67, 22.55, 18.34, 17.29.

EXAMPLE 10

(±)-3-Acetyl-1-(4-amino-3-chlorophenyl)-7-bromo4,5-dihydro-4-methyl-8-methoxy-3H-2,3-benzodiazepine 4.66 g (10 mmoles) of (±)-3-acetyl-7-bromo-4,5-dihydro-1-(3-chloro-4-nitrophenyl)-4-methyl-8-methoxy-3H-2,3-benzodiazepine are dissolved in a mixture of 45 cm$^3$ of methanol and 45 cm$^3$ of dichloromethane, then 3.0 g of wet Raney nickel catalyst and, under vigorous stirring, 1.7 cm$^3$ (35 mmoles) of 98% hydrazine hydrate are added. The reaction mixture is stirred for further 45 minutes, the catalyst is filtered, washed with dichloromethane, the filtrate is evaporated, and the residue is rubbed with 50 cm$^3$ of water to obtain solid matter. The crude product is purified by boiling in 50 ml of acetonitrile. Thus, 3.52 g (81%) of the title compound are obtained in the form of white solids melting at 235–237° C.

Analysis: for C$_{19}$H$_{19}$BrClN$_3$O$_2$ (436.740)

calculated: C 52.25%; H 4.39%; N 9.62%; ΣHlg(Cl) 16.24%.

found: C 51.04%; H 4.34%; N 9.39%; ΣHlg(Cl) 16.16%.

$^1$H-NMR (CDCl$_3$): δ 7.65 (d, J=1.8 Hz, 1H), 7.48 (s, 1H), 7.36 (dd, J$_1$=1.8 Hz, J$_2$=8.3 Hz, 1H), 6.77 (d, J=8.4 Hz, 1H), 6.62 (s, 1H), 5.21 (m, 1H), 4.46 (bs, 2H), 3.77 (s, 3H), 2.77 (dd, J$_1$=5.1 Hz, J$_2$=14.1 Hz, 1H), 2.62 (dd, J$_1$=11.4 Hz, J$_2$=13.9 Hz, 1H), 2.07 (s, 3H), 1.25 (d, J=6.3 Hz, 3H).

$^{13}$C-NMR (CDCl$_3$): δ169.77, 168.18, 154.48, 145.64, 133.71, 133.50, 133.04%, 130.45, 129.25, 126.94, 118.89, 114.81, 114.08, 112.42, 60.48, 56.52, 37.54, 22.74, 1843.

The invention claimed is:

1. A compound of the formula (I)

wherein,

X represents a hydrogen atom, a chloro atom or a methoxy group,

Y stands for hydrogen atom or a halo atom,

Z means a methyl group or a chloro atom,

R is a C$_{1-4}$ alkyl group or a group of the formula —NR$^1$R$^2$, wherein R$^1$ and R$^2$ represent, independently, a hydrogen atom, a C$_{1-4}$ alkyl group, a C$_{1-4}$ alkoxy group or a C$_{3-6}$ cycloalkyl group, and pharmaceutically suitable acid addition salts thereof.

2. The compound according to claim 1, wherein

X represents a chloro atom,

Y stands for a hydrogen atom, a chloro atom or a bromo atom,

R means a C$_{1-4}$ alkyl group, and pharmaceutically acceptable acid addition salts thereof.

3. The compound according to claim 2, wherein

Y represents a hydrogen atom or a chloro atom,

R stands for a methyl group, and pharmaceutically acceptable acid addition salts thereof.

4. A pharmaceutical composition comprising the compound according to claim 1, or a pharmaceutically suitable acid addition salt thereof as the active ingredient in addition to the usual carrier(s).

5. The pharmaceutical composition according to claim 4, wherein in the compound of formula (I), X represents a chloro atom, Y stands for a hydrogen atom, a chloro atom or a bromo atom, R means a C$_{1-4}$ alkyl group.

6. The pharmaceutical composition according to claim 5, wherein in the compound of formula (I), Y represents a hydrogen atom or a chloro atom, R stands for a methyl group.

7. A method of treating diseases and symptoms accompanied by acute and chronic neurodegeneration, which comprises:

administering a therapeutically effective amount of a compound according to claim 1, or a pharmaceutically suitable acid addition salt thereof to a patient in need thereof, wherein said symptoms accompanied by acute and chronic nuerodegeneration comprise symptoms attributable to Parkinson's disease, Alzheimer's disease, amyotrophic lateral sclerosis, stroke, acute head injury, epilepsy, schizophrenia, spasmolysis, emesis, migraine, urination problems or medicine deprivation.

* * * * *